United States Patent [19]

Peifer et al.

[11] Patent Number: 5,712,404
[45] Date of Patent: Jan. 27, 1998

[54] CYCLOPENTADIENYL-TYPE LIGANDS, METALLOCENE COMPOUNDS CATALYST SYSTEMS, PREPARATION AND USE

[75] Inventors: Bernd Peifer; Helmut G. Alt, both of Bayreuth, Germany; M. Bruce Welch, Bartlesville, Okla.

[73] Assignee: Phillips Petroleum Company, Bartlesville, Okla.

[21] Appl. No.: 441,166

[22] Filed: May 15, 1995

[51] Int. Cl.$^6$ ................................................ C09F 17/00
[52] U.S. Cl. ............................ 556/53; 556/43; 526/943; 526/160
[58] Field of Search ............................ 556/11, 53, 43, 556/943

[56] References Cited

U.S. PATENT DOCUMENTS

| | | | |
|---|---|---|---|
| 3,035,075 | 5/1962 | Sweeney | 556/53 X |
| 3,205,257 | 9/1965 | Fritz et al. | 260/465 |
| 3,426,069 | 2/1969 | Fritz | 260/562 |
| 5,191,132 | 3/1993 | Patsidis et al. | 585/375 |
| 5,243,001 | 9/1993 | Winter et al. | 526/127 |
| 5,565,534 | 10/1996 | Aulbach et al. | 526/160 |

OTHER PUBLICATIONS

R.L Morrison and R.N. Boyd, "Organic Chemistry," 3d Ed, p. 318, Allyn & Bacon, Inc., Boston (1973).
R. Grant and C. Grant, eds., "Grant & Hackh's Chemical Dictionary," 5th Ed., p. 14, McGraw-Hill, New York (1987).
The Addition of Grignard Reagents to the Dibiphenylenepolyenes, Fuson, R.C. et al., J. Org. Chem., 16, pp. 21–32 (1951).
Reaction of 9–chloromethylene–Fluorene with Butyl–and Phenyl–Lithiuma Curtin, D.Y. et al., Chemistry and Industry 1453–1454 (1957).
The Reaction of Lithium Aluminum Hydride with Dibiphenyleneethylene, Dibiphenylenebutadiene, and Dibiphenylenebutatriene, Fulvenes and Thermochromic Ethylenes, Part 27, Lavie, D. and Bergman, E.D.,
J. Org. Chem., 18, pp. 367–377 (1953).
Kuhn, R., et al., CA 58:13765g, (1962).
The Acid–catalyzed Reaction of 9–Fluorenol with 9–Alkylidenefluorenes, Wawzonek, S. and Dufek, E., J. Am. Chem. Soc., 78, 3530–3533 (1956).

*Primary Examiner*—Mark Nagumo
*Attorney, Agent, or Firm*—Carl D. Corvin

[57] ABSTRACT

In accordance with the present invention there is provided a process for preparing a cyclopentadienyl-type ligand comprising reacting an alkali metal compound and a fulvene-type compound to form a dianion, and then reacting the dianion with water. In accordance with another embodiment of the present invention a process for preparing a metallocene compound is provided comprising reacting an alkali metal compound, a fulvene-type compound, and a transition metal-containing compound. In another embodiment, the metallocene compound and a cocatalyst are combined to form a catalyst system. Other aspects of the invention include the cyclopentadienyl-type ligands, metallocene compounds, and catalyst systems thus produced and polymerization processes employing the catalyst systems.

24 Claims, No Drawings

CYCLOPENTADIENYL-TYPE LIGANDS, METALLOCENE COMPOUNDS CATALYST SYSTEMS, PREPARATION AND USE

The present invention relates to cyclopentadienyl-type ligands, metallocene compounds, catalyst systems, their preparation and use.

BACKGROUND OF THE INVENTION

As used herein, the term cyclopentadienyl-type ligands includes ligands containing at least two cyclopentadienyl-type groups. Cyclopentadienyl-type groups, as used herein includes groups containing a cyclopentadienyl group, and includes cyclopentadienyl, substituted cyclopentadienyl, indenyl, substituted indenyl, fluorenyl, substituted fluorenyl, tetrahydroindenyl, and octahydrofluorenyl groups.

Cyclopentadienyl-type ligands have found a number of uses in the past. Such ligands have utility in the preparation of metallocene compounds useful for the polymerization of olefins. Other applications for metallocene compounds include asymmetric hydrogenation, alkene epoxidation, alkene isomerization, ketone reduction, and as stoichiometric reagents for stereoselective cobalt-mediated reactions, allyltitanium addition reactions with aldehydes, and the highly selective formation of allylic amines.

It would therefore be desirable to produce a variety of novel ligands from readily available materials employing a simple and economical process. It would also be desirable to produce a variety of such ligands in pure form without byproducts and in high yields from readily available materials employing a simple and economical process. In addition it would be desirable to produce such ligands with a process which does not require isolation of intermediate products, i.e. a one-pot synthesis.

Metallocene catalysts have been used in homogeneous solution polymerizations of olefins. Attempts to use soluble metallocene catalysts in a slurry or particle form type polymerization are currently not commercially feasible. It has been pobserved that when such particle form polymerizations are carried out in the presence of a soluble metallocene catalyst, large amounts of polymeric material are formed on the surfaces of the polymerization vessel. This fouling produces an adverse effect on the heat transfer and also results in the need for periodic, if not continuous, cleaning of the reactor. It would therefore be desirable to produce economical metallocene catalysts useful in polymerization processes free of reactor fouling.

Mother important aspect of olefin polymerization is the activity. By activity is meant the amount or yield of solid polymer that is obtained by employing a given quantity of catalyst in a given amount of time. When the activity is high, catalyst residues do not interfere with the properties of the polymer and therefore the catalyst residues do not need to be removed.

SUMMARY OF THE INVENTION

An object of the present invention is to provide an economical and simple processes for preparing new cyclopentadienyl-type ligands.

Another object of the present invention is to provide a process for preparing such ligands in pure form and high yields.

Another object of the present invention is to provide a one-pot process for preparing metallocene compounds.

Another object of the present invention is to provide a variety of cyclopentadienyl-type ligands useful in preparing metallocene compounds.

Another object of the present invention is to provide various metallocene compounds useful in the polymerization of olefins.

Another object of the present invention is to provide processes for preparing new metallocene compounds.

Another object of the present invention is to provide catalyst systems with high activity capable of polymerizing olefins.

Another object of the present invention is to provide processes for preparing catalyst systems.

Another object of the present invention is to provide olefin polymerization processes free from reactor fouling.

In accordance with the present invention there is provided a process for preparing a cyclopentadienyl-type ligand comprising reacting an alkali metal compound and a fulvene-type compound to form a dianion, and then reacting the dianion and water. Fulvene-type compound as used herein is a compound containing two cyclopentadienyl-type groups which are bridged by a bridging group containing at least one unsaturated carbon—carbon bond attached to at least one cyclopentadienyl-type group. In another embodiment an alkali metal compound, a fulvene-type compound, and a transition metal-containing compound are reacted to form a metallocene compound. In another embodiment the metallocene compound and a cocatalyst are combined to form a catalyst system. Other aspects of the invention include the cyclopentadienyl-type ligands, metallocene compounds, and catalyst systems thus produced and polymerization processes employing the catalyst systems.

DETAILED DESCRIPTION OF THE INVENTION

Cyclopentadienyl-Type Ligands

In the first step of the inventive process, an alkali metal compound is reacted with a fulvene-type compound to produce a bridged dianion having hydrocarbyl substituents on the bridging group.

The fulvene-type compound contains two cyclopentadienyl-type groups which are bridged by a bridging group. Prior to reaction with the alkali metal compound, the bridging group contains from 1 to 12 carbon atoms and at least one unsaturated carbon—carbon bond attached to at least one cyclopentadienyl-type group. Fulvene-type compounds includes compounds containing a cyclopentadienylidene, indenylidene, or fluorenylidene functionality. The bridging group can contain two or three unsaturated carbon—carbon bonds.

Substituted cyclopentadienyl-type groups contain substituents which can be any substitutent which does not interfere with the reactions in the inventive process. Typical substituents include hydrocarbyl groups containing 1 to 12 carbon atoms, alkoxy groups containing 1 to 12 carbon atoms, silyl groups, alkyl halide groups where the alkyl contains 1 to 12 carbon atoms, or halide. Preferably the substituents are alkyl or alkenyl groups containing 1 to 10 carbon atoms, more preferably 1 to 6 carbon atoms.

Some examples of substituents include methyl, ethyl, propyl, butyl, tert-butyl, isobutyl, amyl, isoamyl, hexyl, cyclohexyl, heptyl, octyl, nonyl, decyl, cetyl, dodecyl, 2-ethylhexyl, allyl, butenyl, pentenyl, phenyl, substituted phenyl, phenoxy, methoxy, ethoxy, propoxy, butoxy, phenoxy, dimethylsilyl, trimethylsilyl, chloromethyl, chloroethyl, bromopropyl, chloride, bromide, iodide, and mixtures thereof. Preferably the substituents are alkyl groups containing 1 to 10 carbon atoms, and more preferably 1 to 6 carbon atoms.

Fulvene-type compounds can be prepared by any method known in the art. One method for preparing fulvene-type compounds comprises reacting a bridged cyclopentadienyl-type ligand, α,α'-azo-isobutyronitrile, and N-bromosuccinimide in carbon tetrachloride at reflux temperature. The mixture is mixed with water and the organic phase dried over sodium sulfate. The solvent is removed and the recovered residue is reacted with N,N-dimethylaniline at a temperature in the range of from about 100° C. to about 200° C. to produce the fulvene-type compound.

Methylene-bridged fulvene-type compounds can be prepared by reacting an alkali metal salt of an unbridged cyclopentadienyl-type compound with ethyl formate, followed by acid hydrolysis employing an acid such as hydrochloric acid. The alkali metal salt is prepared by reacting the unbridged cyclopentadienyl-type compound with an alkali metal compound containing a hydrocarbyl group containing 1 to 12 carbon atoms. The reactions are generally conducted in a diluent, such as tetrahydrofuran, and at a temperature in the range of from about −100° C. to about 50° C.

U.S. Pat. No. 5,191,132 and U.S. Pat. No. 5,210,352 disclose the preparation of bridged and unbridged cyclopentadienyl-type compounds which can be employed in preparing the fulvene-type compounds. The disclosures of these patents are incorporated herein by reference.

The alkali metal compounds employed in preparing the dianion can include any alkali metal compounds capable of forming the dianion. Typically the alkali metal compounds would be selected from the hydrocarbyl compounds of sodium, potassium, and lithium and the hydrocarbyl group would contain 1 to 12, preferably 1 to 8 carbon atoms. The preferred alkali metal compounds are lithium alkyls or lithium alkenyls. Due to availability and efficacy, butyllithium and butenyllithium are especially preferred.

Examples of typical alkali metal compounds include methyllithium, ethyllithium, propyllithium, butyllithium, sec-butyllithium, phenyllithium, phenylsodium, methylsodium, ethylsodium, methylpotassium, ethylpotassium, ethenyllithium, propenyllithium, butenyllithium, and mixtures thereof.

In preparing the dianion, the alkali metal compound will be present in an amount in the range of from about 0.1 mole to about 25 moles per mole of fulvene-type compound, preferably from about 1 mole to about 15 moles, more preferably from about 1.5 moles to about 5 moles, and most preferably from about 1.5 to about 2.5 moles alkali metal compound per mole of fulvene-type compound.

The reaction conditions for reacting the alkali metal compound with the fulvene-type compound can vary broadly depending on the particular compounds employed. Generally the temperature will be in the range of from about −78° C. to about 150° C., preferably from about 0° C. to about 125° C., and more preferably from 0° C. to 100° C.

Generally diluents are employed in carrying out the various steps of the present invention. Typical diluents include polar diluents such as for example tetrahydrofuran, or non-polar diluents such as alkanes, cycloalkanes, aromatic hydrocarbons, and non-cyclic ethers. Some specific examples of nonpolar diluents include toluene, heptane, hexane, dichloromethane, and diethylether.

The dianion can be reacted with water to produce a stable cyclopentadienyl-type ligand or can be reacted with a transition metal-containing compound to form a metallocene compound.

When reacting the dianion with water, improved yields are obtained by employing reduced temperatures and slowly combining the water and the dianion. For example, a reaction mixture of the dianion can be cooled with ice and the water added dropwise. In another method, the reaction mixture containing the dianion can also be added dropwise to ice water. Preferably the temperature does not exceed 20° C. during this step and more preferably the temperature is less than 15° C. Typically the cyclopentadienyl-type ligand can be extracted with a solvent such as pentane, dried over sodium sulfate, and then recovered by evaporation of the solvent or recrystallization.

Generally water will be employed in an amount in the range of from about 0.2 mole to about 50 moles per mole of dianion, preferably from about 0.5 mole to about 20 moles per mole, and more preferably from 1 mole to 10 moles per mole of dianion.

The stable cyclopentadienyl-type ligand is represented by the formula

wherein each Z is individually selected and is a cyclopentadienyl-type group, wherein Q is a bridging group containing from 1 to 12 carbon atoms, wherein each R is individually selected from the group consisting of hydrogen and hydrocarbyl groups containing from 1 to 12 carbon atoms, and wherein m is 2 to 24.

Metallocene Compounds

When preparing the metallocene compound, the dianion is reacted with a transition metal-containing compound. The transition metal-containing compound is represented by the formula $MX_x$, wherein M is a Group IVB or VB transition metal, preferably titanium, zirconium, hafnium, or vanadium, more preferably titanium, zirconium or hafnium, x is the valence of the transition metal, and each X is individually selected from the group consisting of hydrocarbyl groups containing 1 to 12 carbon atoms, alkoxy groups containing 1 to 12 carbon atoms, aryloxy groups containing 6 to 12 carbon atoms, halide and hydride. Preferably X is a halide, more preferably X is chloride.

Some examples of such transition metal-containing compounds include, zirconium tetrachloride, zirconium tetrabromide, zirconium tetraiodide, zirconium tetramethoxide, zirconium tetraethoxide, zirconium tetrapropoxide, zirconium tetrabutoxide, methylzirconium trichloride, hafnium tetrachloride, hafnium tetrabromide, hafnium tetraiodide, hafnium tetramethoxide, hafnium tetraethoxide, hafnium tetrapropoxide, hafnium tetrabutoxide, titanium trichloride, titanium tetrachloride, titanium tetrabromide, titanium tetraiodide, titanium tetramethoxide, titanium tetraethoxide, titanium tetrapropoxide, titanium tetrabutoxide, vanadium tetrachloride, vanadium tetraiodide, vanadium tetramethoxide, vanadium tetraethoxide, vanadium tetrapropoxide, and vanadium tetrabutoxide. Excellent results have been obtained with zirconium tetrachloride and hafnium tetrachloride and they are preferred.

Generally the transition metal-containing compound will be present in an amount in the range of from about 0.1 mole to about 50 moles per mole of dianion, preferably from about 0.2 mole to about 20 moles per mole, and more preferably from 0.5 mole to 10 moles per mole of dianion.

The reaction conditions for reacting the dianion with the transition metal-containing compound can vary depending on the particular compounds employed. Generally the temperature will be in the range of from about −78° C. to about 150° C., preferably from about 0° C. to about 125° C., and more preferably from 0° C. to 100° C.

Generally diluents are employed when reacting the dianion and the transition metal-containing compound. Typical diluents include polar diluents such as for example tetrahydrofuran, or non-polar diluents such as alkanes, cycloalkanes, aromatic hydrocarbons, and non-cyclic ethers. Some specific examples of nonpolar diluents include toluene, heptane, hexane, dichloromethane, and diethylether.

The metallocene compound is represented by the formula

$$\underset{\underset{R_m}{|}}{ZQZMX_2}$$

wherein each Z is individually selected and is a cyclopentadienyl-type group, wherein Q is a bridging group containing from 1 to 12 carbon atoms, wherein M is a Group IVB or VB transition metal, wherein each X is individually selected from the group consisting of hydrocarbyl groups containing 1 to 12 carbon atoms, alkoxy groups containing 1 to 12 carbon atoms, aryloxy groups containing 6 to 12 carbon atoms, halide and hydride, wherein each R is individually selected from the group consisting of hydrogen and hydrocarbyl groups containing from 1 to 12 carbon atoms, and wherein m is 2 to 24.

Examples of typical metallocene compounds which can be prepared by the inventive process include
bis(9-fluorenyl)(methyl)methane zirconium dichloride,
bis(9-fluorenyl)(ethyl)methane zirconium dichloride,
bis(9-fluorenyl)(propyl)methane zirconium dichloride,
bis(9-fluorenyl)(butyl)methane zirconium dichloride,
bis(9-fluorenyl)(phenyl)methane zirconium dichloride,
(cyclopentadienyl)(1-indenyl)(methyl)methane zirconium dichloride,
(cyclopentadienyl)(9-fluorenyl)(ethyl)methane zirconium dichloride,
(1-indenyl)(9-fluorenyl)(propyl)methane zirconium dichloride,
bis(1-indenyl)(butyl)methane zirconium dichloride,
bis(cyclopentadienyl)(phenyl)methane zirconium dichloride,
(butyl)(cyclopentadienyl)(9-fluorenyl)methane zirconium dichloride,
((but-3-enyl)(9-fluorenyl)(1-indenyl)methane zirconium dichloride,
1,2-bis(9-fluorenyl)(1,2-dimethyl)ethane zirconium dichloride,
1,2-bis(9-fluorenyl)(1,2-diethyl)ethane zirconium dichloride,
1,2-bis(9-fluorenyl)(1,2-dipropyl)ethane zirconium dichloride,
1,2-bis(9-fluorenyl)(1,2-dibutyl)ethane zirconium dichloride,
1,2-bis(9-fluorenyl)(1,2-diphenyl)ethane zirconium dichloride,
1,2-bis(9-fluorenyl)(1,2-dibutyl)ethane zirconium dibromide,
bis(9-fluorenyl)(methyl)methane zirconium diiodide,
1,2-bis(9-(4-methylfluorenyl))(1,2-dipropyl)ethane zirconium dichloride,
bis(9-(1-tert-butylfluorenyl))(butyl)methane zirconium dichloride,
bis(9-fluorenyl)(methyl)methane hafnium dichloride,
bis(9-fluorenyl)(ethyl)methane hafnium dichloride,
1,2-bis(9-fluorenyl)(1,2-dipropyl)ethane hafnium dibromide,
1,2-bis(9-fluorenyl)(1,2-dibutyl)ethane hafnium diiodide,
bis(9-(4-methylfluorenyl))(phenyl)methane hafnium dichloride,
1,2-bis(9-(4-t-butylfluorenyl))(1,2-dipentyl)ethane hafnium dichloride,
1,2-bis(9-fluorenyl)(1,2-diheptyl)ethane titanium dichloride,
1,2-bis(9-(4-methylfluorenyl))(1,2-dimethyl)ethane titanium dichloride,
1,2-bis(9-(4-tert-butylfluorenyl)(1,2-dipropyl)ethane titanium dichloride,
bis(9-fluorenyl)(butenyl)methane zirconium methyl chloride,
bis(9-(2,7-di-tert-butylfluorenyl))(phenyl)methane zirconium ethyl chloride,
bis(9-(4-methylfluorenyl))(methyl)methane zirconium phenyl chloride,
bis(9-fluorenyl)(butyl)methane hafnium methyl chloride,
bis(9-(1-methylfluorenyl))(propenyl)methane hafnium ethyl chloride,
1,2-bis(9-(4-n-butylfluorenyl))(1,2-diethyl)ethane hafnium phenyl chloride,
1,2-bis(9-fluorenyl)(1,2-dibutenyl)methane titanium methyl chloride,
bis(9-(2,7-dimethylfluorenyl))(1-heptenyl)methane titanium ethyl chloride,
bis(9-(1-n-butylfluorenyl))(pentyl)methane titanium phenyl chloride,
1,2-bis(9-fluorenyl)(1,2-dipropyl)ethane zirconium dimethyl,
bis(9-(4-methylfluorenyl))(phenyl)methane zirconium dimethyl,
bis(9-(4-n-butylfluorenyl))(methyl)methane zirconium dimethyl,
bis(9-fluorenyl)(ethyl)methane hafnium dimethyl,
1,2-bis(9-(2,7-dimethylfluorenyl))(1,2-dibutyl)ethane hafnium dimethyl,
bis(9-(1-n-butylfluorenyl))(butyl)methane hafnium dimethyl,
bis(9-fluorenyl)(octyl)methane titanium dimethyl,
bis(9-(4-methylfluorenyl))(hexyl)methane titanium dimethyl,
1,2-bis(9-(2,7-di-t-butylfluorenyl)(dibutenyl)ethane titanium dimethyl, and mixtures thereof.

Generally, cocatalysts, such as organoaluminoxanes, are employed with the metallocene compounds to produce a catalyst system. Various techniques are known for making organoaluminoxanes. One technique involves the controlled addition of water to a trialkylaluminum. Another technique involves combining a trialkylaluminum and a hydrocarbon with a compound containing water of adsorption or a salt containing water of crystallization. Many suitable organoaluminoxanes are commercially available.

Typically the organoaluminoxanes comprise oligomeric, linear and/or cyclic hydrocarbyl aluminoxanes having repeating units of the formula

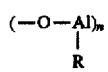

wherein each R is a hydrocarbyl group, preferably an alkyl group containing 1–8 carbon atoms, n is 2 to 50, preferably 4 to 40, more preferably 10 to 40. Typically R is predominantly methyl or ethyl. Preferably at least about 30 mole percent of the repeating groups have an R which is methyl, more preferably at least 50 mole percent, and still more preferably at least 70 mole percent. Generally in the preparation of an organoaluminoxane, a mixture of linear and cyclic compounds is obtained. Organoaluminoxanes are commercially available in the form of hydrocarbon solutions, generally aromatic hydrocarbon solutions. Typically such organoaluminoxane solutions contain trialkylaluminum compounds as well as the oligomeric organoaluminoxane. The trialkylaluminum compounds generally include those in which the alkyl groups contain 1 to 12 carbon atoms, preferably 1 to 8 carbon atoms.

A solid organoaluminoxy product can be prepared by reacting an organoaluminoxane and an oxygen-containing compound selected from the group consisting of organo boroxines, organic boranes, organic peroxides, alkylene oxides, and organic carbonates. Organo boroxines are preferred.

If an alkenyl substituent is present, the catalyst system can be prepolymerized at least once in the presence of a limiting amount of at least one olefin to form a solid catalyst system. The prepolymerized catalyst system can be washed and prepolymerized again with at least one olefin. Generally the olefin will contain from 2 to 24 carbon atoms, preferably from 2 to 18 carbon atoms, and more preferably from 2 to 12 carbon atoms. Suitable olefins include ethylene, propylene, 1-butene, 1-pentene, 2-pentene, 3-methyl-1-butene, 4-methyl-1-pentene, 1-hexene, 2-hexene, cyclohexene, 1-heptene, dienes such as 1,3-butadiene, cyclopentene, cyclooctene, norbornene, tetracyclododecene, and mixtures thereof. Ethylene is preferred.

Typically the prepolymerization will be conducted at relatively low temperature and pressure. Generally the prepolymerization will be conducted at a temperature in the range of about −100° C. to about 200° C., preferably in the range of about −40° C. to about 100° C. The prepolymerized solid catalyst system can be filtered, washed, and dried under vacuum.

The amount of prepolymer can vary broadly but generally will be in the range of from about 1 to about 95 weight percent based on the total prepolymerized catalyst system, preferably in the range of about 5 to about 80 weight percent. Preferably the prepolymer will be present in an amount sufficient to form a solid catalyst system.

The amount of organoaluminoxane relative to the metallocene compound can vary broadly depending upon the particular catalyst selected and the results desired. Typically, the organoaluminoxane will be present in the amount of about 0.1 mole to about 10,000 moles per mole of metallocene compound, preferably about 1 moles to about 5,000 moles, and more preferably 5 moles to 1,000 moles.

Other cocatalysts can also be employed in the catalyst systems. Examples of suitable cocatalysts include any of those organometallic cocatalysts which have in the past been employed in conjunction with transition metal-containing olefin polymerization catalysts. Some typical examples include organometallic compounds of metals of Groups IA, IIA, and IIIB of the Periodic Table. Examples of such compounds include organometallic halide compounds, organometallic hydrides, and metal hydrides. Some specific examples include triethylaluminum, tri-isobutylaluminum, diethylaluminum chloride, diethylaluminum hydride, and the like. Other examples of known cocatalysts include the use of compounds capable of forming a stable non-coordinating counter anion, such as disclosed in U.S. Pat. No. 5,155,080, e.g. using triphenyl carbenium tetrakis (pentafluorophenyl)boronate or tris(pentaflurophenyl)boron. Another example would be the use of a mixture of trimethylaluminum and dimethylfluoroaluminum such as disclosed by Zambelli et, *Macromolecules*, 22, 2186 (1989).

Polymerization Processes

The catalyst system is useful in the polymerization of olefin compounds. The catalyst system is contacted with at least one olefin under polymerization conditions. A variety of olefin compounds are suitable for use as monomers in the polymerization process of the present invention. Olefins which can be employed include aliphatic linear, branched, cyclic, and aromatic olefins. Olefins having 2 to 24 carbon atoms are most often used, preferably 2 to 18 carbon atoms. Ethylene and propylene are especially preferred. Often a second or third such olefin (comonomer) is employed. Typical polymerizable olefins include ethylene, propylene, 1-butene, 1-pentene, 3-methyl-1-butene, 4-methyl-1-pentene, 1-hexene, 2-hexene, cyclohexene, 1-heptene, 1-octene, styrene, cyclopentene, cyclooctene, norbornene, tetracyclododecene, methyltetracyclododecene, dienes such as 1,3-butadiene, and mixtures thereof.

The reaction conditions for contacting the olefin and the catalyst system can vary broadly depending on the olefin employed, and are those sufficient to polymerize the olefins. Generally the temperature is in the range of about 0° C. to about 300° C., preferably in the range of 50° C. to 150° C. The pressure is generally in the range of from about 0.1 MPa to about 10.0 MPa (14–1500 psi).

The polymerization processes according to the present invention can be performed either batchwise or continuously. The olefin, metallocene compound, and cocatalyst can be contacted in any order. A diluent such as isobutane is generally employed. The reactor is heated to the desired reaction temperature and olefin, such as ethylene, is then admitted and maintained at a partial pressure within a range of from about 0.1 MPa to about 5.0 MPa (14–725 psi) for best results. Hydrogen can be employed to control molecular weight. At the end of the designated reaction period, the polymerization reaction is terminated and the unreacted olefin and diluent can be vented. The reactor can be opened and the polymer can be collected as a free-flowing white solid and dried to obtain the product.

The olefin polymers produced with the present invention are useful in preparing articles prepared by conventional polyolefin processing techniques, such as injection molding, rotational molding, film extrusion, pipe extrusion, and blow molding.

The following examples will serve to show the present invention in detail by way of illustration and not by way of limitation.

EXAMPLES

Examples 1–2 demonstrate the effectiveness of the inventive process in preparing cyclopentadienyl-type ligands. Example 3 demonstrates the preparation of metallocene compounds useful as polymerization catalysts. Example 4 demonstrates the use of the metallocene compounds in catalyst systems employed in polymerizing olefins.

Example 1

Preparation of Ethylene Bridged Fulvene-type Compound

The fulvene-type compound, 1,2-bis(9-fluorenylidene) ethane, was prepared by reacting a solution of 10.00 g (27.90 mmol) 1,2-bis(9-fluorenyl)ethane, 0.50 g (3.04 mmol) α,α'-azo-isobutyronitrile (AIBN) and 10.92 g (61.37 mmol) N-bromosuccinimide, and 150 mL carbon tetrachloride. The reaction mixture was stirred overnight under reflux. The reaction mixture was mixed with 150 mL water. The organic phase was dried over sodium sulfate, and the solvent was evaporated under vacuum. The residue was mixed with 50 mL N,N-dimethylaniline and stirred for one hour at 150° C. The mixture was filtered and the recovered orange solid was washed twice with 100 mL diethyl ether and dried under vacuum. The yield of the thus produced 1,2-bis(9-fluorenylidene)ethane was 60%.

Example 2

Preparation of Methylene Bridged Fulvene-type Compound

The fulvene-type compound difluorenylidenemethane, was prepared by reacting two equivalents of fluorenyl-lithium with ethyl formate. After acid hydrolysis, difluorenylidenemethane was recovered.

To a solution of 20.00 g (120.32 mmol) fluorene in 150 mL THF was added 75.2 mL (120.32 mmol) 1.6M solution of n-butyllithium in hexane at −78° C. The reaction mixture was allowed to come to room temperature and was stirred overnight. The mixture was cooled to −78° C. and 4.84 mL (60.16 mmol) ethyl formate was added. The reaction mixture was allowed to come to room temperature and was stirred for 4 hours. The 50 mL concentrated hydrochloric acid were added slowly. The organic layer was separated, the solvent was evaporated in vacuo and the residue was washed with 50 mL diethyl ether followed by 100 mL pentane. The thus produced difluorenylidenemethane was a white crystalline powder which was dried under vacuum. The yield of difluorenylidenemethane was 50%.

Example 3

Preparation of Metallocene Compounds

Metallocene compounds were prepared by reacting an alkali metal compound and the fulvene-type compounds prepared as described above to form a dianion and reacting the dianion with a transition metal-containing compound. The dianion was prepared by dissolving 3.00 mmol fulvene-type compound in 100 mL diethyl ether and mixed at room temperature with 3.75 mL (6.00 mmol) n-butyllithium. The reaction mixture was stirred overnight at room temperature. To the reaction mixture containing the dianion was added 0.70 g (3.00 mmol) zirconium tetrachloride or 0.96 g hafnium tetrachloride. The reaction mixture was stirred for at least four hours at room temperature. The reaction mixture was then filtered over sodium sulfate, and the residue was extracted with methylene chloride. The thus produced metallocene compounds were crystallized from chloroform at −25° C. Yields of bis(fluorenyl)(butyl)methane zirconium dichloride and (1,2-bis(9-fluorenyl))(1,2-dibutyl)ethane zirconium dichloride were 60–70%.

Example 4

Polymerization

Example 4 demonstrates the effectiveness of the above prepared metallocene compounds to polymerize ethylene. Catalyst systems were prepared by reacting at room temperature the indicated amount of metallocene compound with 10 mL methylaluminoxane (1.1M in toluene) (MAO).

TABLE 1

| Catalyst System | MAO | Metallocene Compound |
|---|---|---|
| A | 10 mL | 0.0126 g (butyl)(difluorenyl)methanezirconium dichloride |
| B | 10 mL | 0.0152 g (butyl)(difluorenyl)methanehafnium dichloride |
| C | 10 mL | 0.0140 g (1,2-bis(9-fluorenyl))(1,2-dibutyl)ethanezirconium dichloride |
| D | 10 mL | 0.0158 g (1,2-bis(9-fluorenyl))(1,2-dibutyl)ethanehafnium dichloride |

Ethylene was polymerized in a 1-gallon stirred autoclave reactor employing the indicated amount of catalyst system. The polymerization was conducted in 2 liters isobutane diluent at a temperature of 90° C., a total pressure of 450 psig, in the presence of hydrogen for one hour. After the polymerization was complete, the isobutane was removed and the polymer collected as a dry fluff.

The results are tabulated in the table below. Catalyst is the mL of catalyst system employed. Yield is the polymer yield in grams. MI is the melt index in grams/10 minutes measured according to ASTM 1238, Condition E. HLMI is the high load melt index in grams/10 minutes measured according to ASTM 1238, Condition F. Density is the polymer density in grams/cc measured according to ASTM D 1505.

TABLE 2

| Catalyst mL | Hexene grams | Yield grams | MI g/10 min. | HLMI g/10 min. | Density g/cc |
|---|---|---|---|---|---|
| 1.5 mL A | 0 | 88.68 | 0 | 0 | 0.9364 |
| 1.5 mL A | 40 | 99.58 | 0.3539 | 28.55 | 0.9152 |
| 1.5 mL B | 0 | 0.7 | — | — | — |
| 1.5 mL B | 40 | 0.36 | — | — | — |
| 1.5 mL C | 0 | 198.84 | 0 | 3.508 | 0.9551 |
| 1.5 mL C | 40 | 241.79 | 0 | 0 | 0.9164 |
| 2.0 mL D | 0 | 25.13 | 0 | 2.626 | 0.9585 |
| 2.0 mL D | 40 | 37.12 | 0 | 61.33 | 0.9079 |

—did not measure

The results in Table 2 indicate especially high yields for the catalyst system containing (1,2-bis(9-fluorenyl))(1,2-dibutyl)ethanezirconium dichloride.

That which is claimed is:

1. A process for preparing a metallocene compound said process comprising reacting a fulvene-type compound, an alkali metal compound, and a transition metal-containing compound:

wherein said fulvene-type compound contains two cyclopentadienyl-type groups, wherein said cyclopentadienyl-type groups which are bridged by a bridging group, wherein said bridging group contains at least one unsaturated carbon—carbon bond, and wherein said at least one unsaturated carbon—carbon bond is attached to at least one of said cyclopentadienyl-type groups, and wherein said bridging group reacts to form an aliphatic acyclic structural connection between said two cyclopentadienyl-type groups, wherein said cyclopentadienyl-type groups are cyclopentadienyl, substituted cyclopentadienyl, indenyl, substituted indenyl, fluorenyl, substituted fluorenyl, tetrahydroindenyl, or octahydrofluorenyl groups, wherein said substituents are hydrocarbyl groups containing 1 to 12 carbon atoms, alkoxy groups containing 1 to 12 carbon atoms, silyl groups, alkyl halide groups where said alkyl contains 1 to 12 carbon atoms, or halide;

wherein said alkali metal compound is a hydrocarbyl compound of sodium, potassium, or lithium, wherein said hydrocarbyl group contains from 1 to 12 carbon atoms; and wherein said transition metal-containing compound is represented by the formula $MX_x$, wherein M is a Group IVB or VB transition metal, each X is individually selected from the group consisting of hydrocarbyl groups containing 1 to 12 carbon atoms, alkoxy groups containing 1 to 12 carbon atoms, aryloxy groups containing 6 to 12 carbon atoms, halide and hydride, and x is the valence of the transition metal.

2. A process according to claim 1 wherein M is titanium, zirconium, hafnium, or vanadium.

3. A process according to claim 2 wherein X is a halide.

4. A process according to claim 3 wherein X is chloride.

5. A process according to claim 4 wherein the transition metal-containing compound is zirconium tetrachloride or hafnium tetrachloride.

6. A process according to claim 5 wherein the fulvene-type compound, the alkali metal compound, and the transition metal-containing compound are reacted at a temperature in the range of from about −78° C. to about 150° C.

7. A process for preparing a metallocene compound said process comprising reacting a fulvene-type compound, an alkali metal compound, and a transition metal-containing compound:

wherein said fulvene-type compound contains two cyclopentadienyl-type groups, and wherein said cyclopentadienyl-type groups are bridged by a bridging group, and wherein said bridging group contains at least one unsaturated carbon—carbon bond, and wherein said at least one unsaturated carbon—carbon bond is attached to at least one of said cyclopentadienyl-type groups, and wherein said cyclopentadienyl-type groups are fluorenyl, substituted fluorenyl or octahydrofluorenyl groups, and wherein said substituents are hydrocarbyl groups containing 1 to 12 carbon atoms, alkoxy groups containing 1 to 12 carbon atoms, silyl groups, alkyl halide groups where said alkyl contains 1 to 12 carbon atoms, or halide; and wherein said alkali metal compound is a hydrocarbyl compound of sodium, potassium, or lithium, and wherein said hydrocarbyl group contains from 1 to 12 carbon atoms; and wherein said transition metal-containing compound is represented by the formula $MX_x$, and wherein M is a Group IVB or VB transition metal, each X is individually selected from the group consisting of hydrocarbyl groups containing 1 to 12 carbon atoms, alkoxy groups containing 1 to 12 carbon atoms, aryloxy groups containing 6 to 12 carbon atoms, halide and hydride, and x is the valence of the transition metal.

8. A process according to claim 7 wherein M is titanium, zirconium, hafnium, or vanadium.

9. A process according to claim 8 wherein X is a halide.

10. A process according to claim 9 wherein X is chloride.

11. A process according to claim 10 wherein the transition metal-containing compound is zirconium tetrachloride or hafnium tetrachloride.

12. A process according to claim 11 wherein said fulvene-type compound, said alkali metal compound, and said transition metal-containing compound are reacted at a temperature in the range of from about −78° C. to about 150° C.

13. A process for preparing a metallocene compound said process comprising reacting a fulvene-type compound, an alkali metal compound, and a transition metal-containing compound:

wherein said fulvene-type compound contains two cyclopentadienyl-type groups, and wherein said cyclopentadienyl-type groups are bridged by a methylene bridging group, and wherein said bridging group contains at least one unsaturated carbon—carbon bond, and wherein said at least one unsaturated carbon—carbon bond is attached to at least one of said cyclopentadienyl-type groups, and wherein said cyclopentadienyl-type groups are cyclopentadienyl, substituted cyclopentadienyl, indenyl, substituted indenyl, fluorenyl, substituted fluorenyl tetrahydroindenyl, or octahydrofluorenyl groups, wherein said substituents are hydrocarbyl groups containing 1 to 12 carbon atoms, alkoxy groups containing 1 to 12 carbon atoms, silyl groups, alkyl halide groups where said alkyl contains 1 to 12 carbon atoms, or halide; and wherein said alkali metal compound is a hydrocarbyl compound of sodium, potassium, or lithium, and wherein said hydrocarbyl group contains from 1 to 12 carbon atoms; and wherein said transition metal-containing compound is represented by the formula $MX_x$, and wherein M is a Group IVB or VB transition metal, each X is individually selected from the group consisting of hydrocarbyl groups containing 1 to 12 carbon atoms, alkoxy groups containing 1 to 12 carbon atoms, aryloxy groups containing 6 to 12 carbon atoms, halide and hydride, and x is the valence of the transition metal.

14. A process according to claim 13 wherein M is titanium, zirconium, hafnium, or vanadium.

15. A process according to claim 14 wherein X is a halide.

16. A process according to claim 15 wherein X is chloride.

17. A process according to claim 16 wherein the transition metal-containing compound is zirconium tetrachloride or hafnium tetrachloride.

18. A process according to claim 17 wherein said fulvene-type compound, said alkali metal compound, and said transition metal-containing compound are reacted at a temperature in the range of from about −78° C. to about 150° C.

19. A process for preparing a metallocene compound said process comprising reacting a fulvene-type compound, an alkali metal compound, and a transition metal-containing compound:

wherein said fulvene-type compound contains two cyclopentadienyl-type groups, and wherein said cyclopentadienyl-type groups are bridged by a methylene bridging group, and wherein said bridging group contains at least one unsaturated carbon—carbon bond, and wherein said at least one unsaturated carbon—carbon bond is attached to at least one of said cyclopentadienyl-type groups, and wherein said cyclopentadienyl-type groups are fluorenyl, substituted fluorenyl or octahydrofluorenyl groups, and wherein said substituents are hydrocarbyl groups containing 1 to 12 carbon atoms, alkoxy groups containing 1 to 12 carbon atoms, silyl groups, alkyl halide groups where said alkyl contains 1 to 12 carbon atoms, or halide; and wherein said alkali metal compound is a hydrocarbyl compound of sodium, potassium, or lithium, and wherein said hydrocarbyl group contains from 1 to 12 carbon atoms; and wherein said transition metal-containing compound is represented by the formula $MX_x$, and wherein M is a Group IVB or VB transition metal, each X is individually selected from the group consisting of hydrocarbyl groups containing 1 to 12 carbon atoms, alkoxy groups containing 1 to 12 carbon atoms, aryloxy groups containing 6 to 12 carbon atoms, halide and hydride, and x is the valence of the transition metal.

20. A process according to claim 19 wherein M is titanium, zirconium, hafnium, or vanadium.

21. A process according to claim 20 wherein X is a halide.

22. A process according to claim 21 wherein X is chloride.

23. A process according to claims 22 wherein the transition metal-containing compound is zirconium tetrachloride or hafnium tetrachloride.

24. A process according to claim 23 wherein said fulvene-type compound, said alkali metal compound, and said transition metal-containing compound are reacted at a temperature in the range of from about −78° C. to about 150° C.

* * * * *

UNITED STATES PATENT AND TRADEMARK OFFICE
CERTIFICATE OF CORRECTION

PATENT NO. : 5,712,404

DATED : January 27, 1998

INVENTOR(S) : Bernd Peifer, Helmut Alt, Bruce Welch

It is certified that error appears in the above-identified patent and that said Letters Patent is hereby corrected as shown below:

Column 12, Claim 13, Line 17, insert ---,--- after fluorenyl.

Signed and Sealed this

Thirteenth Day of October 1998

Attest:

BRUCE LEHMAN

Attesting Officer

Commissioner of Patents and Trademarks